United States Patent
Mikami (10) Patent No.: US 10,517,465 B2
(45) Date of Patent: Dec. 31, 2019

(54) CABLE CONNECTION STRUCTURE AND ENDOSCOPE APPARATUS

(71) Applicant: OLYMPUS CORPORATION, Tokyo (JP)

(72) Inventor: Masato Mikami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 404 days.

(21) Appl. No.: 15/358,330

(22) Filed: Nov. 22, 2016

(65) Prior Publication Data

US 2017/0071453 A1 Mar. 16, 2017

Related U.S. Application Data

(63) Continuation of application No. PCT/JP2015/066942, filed on Jun. 11, 2015.

(30) Foreign Application Priority Data

Jun. 20, 2014 (JP) .................................. 2014-127359

(51) Int. Cl.
*A61B 1/00* (2006.01)
*H05K 1/11* (2006.01)

(52) U.S. Cl.
CPC ...... *A61B 1/00124* (2013.01); *A61B 1/00114* (2013.01); *H05K 1/113* (2013.01)

(58) Field of Classification Search
CPC ............ A61B 1/00124; A61B 1/00096; A61B 1/00114; A61B 1/051; H05K 1/113;
(Continued)

(56) References Cited

U.S. PATENT DOCUMENTS

2004/0057220 A1* 3/2004 Tamaki .................. H01P 5/085
361/760
2004/0072468 A1* 4/2004 Engquist .............. H01R 9/0515
439/493

(Continued)

FOREIGN PATENT DOCUMENTS

JP 2009-158668 A 7/2009
JP 2010-069231 A 4/2010
(Continued)

OTHER PUBLICATIONS

International Search Report dated Sep. 15, 2015 issued in PCT/JP2015/066942.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

A cable connection structure includes: a cable having a core and a jacket made of an insulating material to cover the core; and a substrate connected with the cable. The substrate includes: a base material made of an insulating material; an external connection electrode formed on a surface of the base material and connected with the core; and a via provided in the base material and having an end exposed from a mounting surface of the substrate on which the cable is mounted, the via being connected with the external connection electrode. The via is provided at least at one of both ends of a surface of the external connection electrode perpendicular to an axial direction of the cable, on a proximal end side of the cable.

6 Claims, 9 Drawing Sheets (58) Field of Classification Search
CPC ........ H05K 1/117; H05K 3/32; H05K 3/3452; H05K 2201/09809; H05K 2201/09909; H05K 2201/10356; H05K 1/114; H05K 1/115; H05K 1/112; G02B 23/2423; G02B 23/2476
See application file for complete search history.

(56) References Cited

U.S. PATENT DOCUMENTS

| | | | |
|---|---|---|---|
| 2006/0043570 A1* | 3/2006 | Muramatsu | ........... H01L 21/486 257/698 |
| 2010/0073470 A1 | 3/2010 | Takasaki | |
| 2010/0308451 A1* | 12/2010 | Kodani | ................... H01L 25/16 257/690 |
| 2012/0008294 A1* | 1/2012 | Minoo | ................... H05K 1/183 361/764 |

FOREIGN PATENT DOCUMENTS

| | | | | | |
|---|---|---|---|---|---|
| JP | 2011-049205 A | | 3/2011 | | |
| JP | 2011-071036 A | | 4/2011 | | |
| JP | 2011071036 A | * | 4/2011 | | |
| JP | 2012227293 A | * | 11/2012 | ........... | H01L 33/486 |

* cited by examiner

ALIGNMENT DIRECTION

AXIAL DIRECTION

CABLE CONNECTION STRUCTURE AND ENDOSCOPE APPARATUS

CROSS REFERENCES TO RELATED APPLICATIONS

This application is a continuation of PCT international application Ser. No. PCT/JP2015/066942, filed on Jun. 11, 2015 which designates the United States, incorporated herein by reference, and which claims the benefit of priority from Japanese Patent Application No. 2014-127359, filed on Jun. 20, 2014, incorporated herein by reference.

BACKGROUND

1. Technical Field

The disclosure relates to a cable connection structure and an endoscope apparatus.

2. Related Art

In a medical endoscope, an insertion section is inserted deep inside a body for observation of a lesion, and further a treatment instrument is combined if necessary to inspect and treat inside the body. Such an endoscope includes an image sensor such as a CCD at a distal end of the insertion section, and outputs data from the image sensor to an external control device or the like, through a cable connected to an electrode on a substrate. The endoscope has a distal end portion bendable upward and downward, and rightward and leftward owing to connection of a bending section bendable in a plurality of directions, but a stress is applied to a connection portion between the electrode and the cable due to the movement of the bending section, and the connection portion is required to have a high adhesion strength. Commonly, when a large load is applied to the connection portion, the electrode to which the cable is connected is separated from the substrate. Therefore, a technique for improving the connection strength between the electrode and the substrate has been longed for.

As a technique for improving the adhesion strength between the electrode and the substrate, a technique is disclosed for forming a solid solution including copper and nickel, on an exposed surface of a via formed in a substrate and including a high melting point metal, to improve the adhesion strength to an electrode mainly including copper (e.g., see JP 2009-158668 A).

SUMMARY

In some embodiments, a cable connection structure includes: a cable having a core and a jacket made of an insulating material to cover the core; and a substrate connected with the cable. The substrate includes: a base material made of an insulating material; an external connection electrode formed on a surface of the base material and connected with the core; and a via provided in the base material and having an end exposed from a mounting surface of the substrate on which the cable is mounted, the via being connected with the external connection electrode. The via is provided at least at one of both ends of a surface of the external connection electrode perpendicular to an axial direction of the cable, on a proximal end side of the cable.

In some embodiments, an endoscope apparatus includes an imaging device configured to be inserted into a living body to image an inside of the living body. The imaging device includes the cable connection structure.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiment(s)") will be described below with reference to the accompanying drawings. It should be understood that the present invention is not limited to these embodiments. The same reference signs are used to designate the same elements throughout the drawings. Note that each of the drawings is schematically illustrated, and a relationship between the thickness and the width of each member, the proportion or the like of each member may be different from those of actual one. The dimensional relationship or proportion may be partially different between the drawings.

First Embodiment

Figure 1:
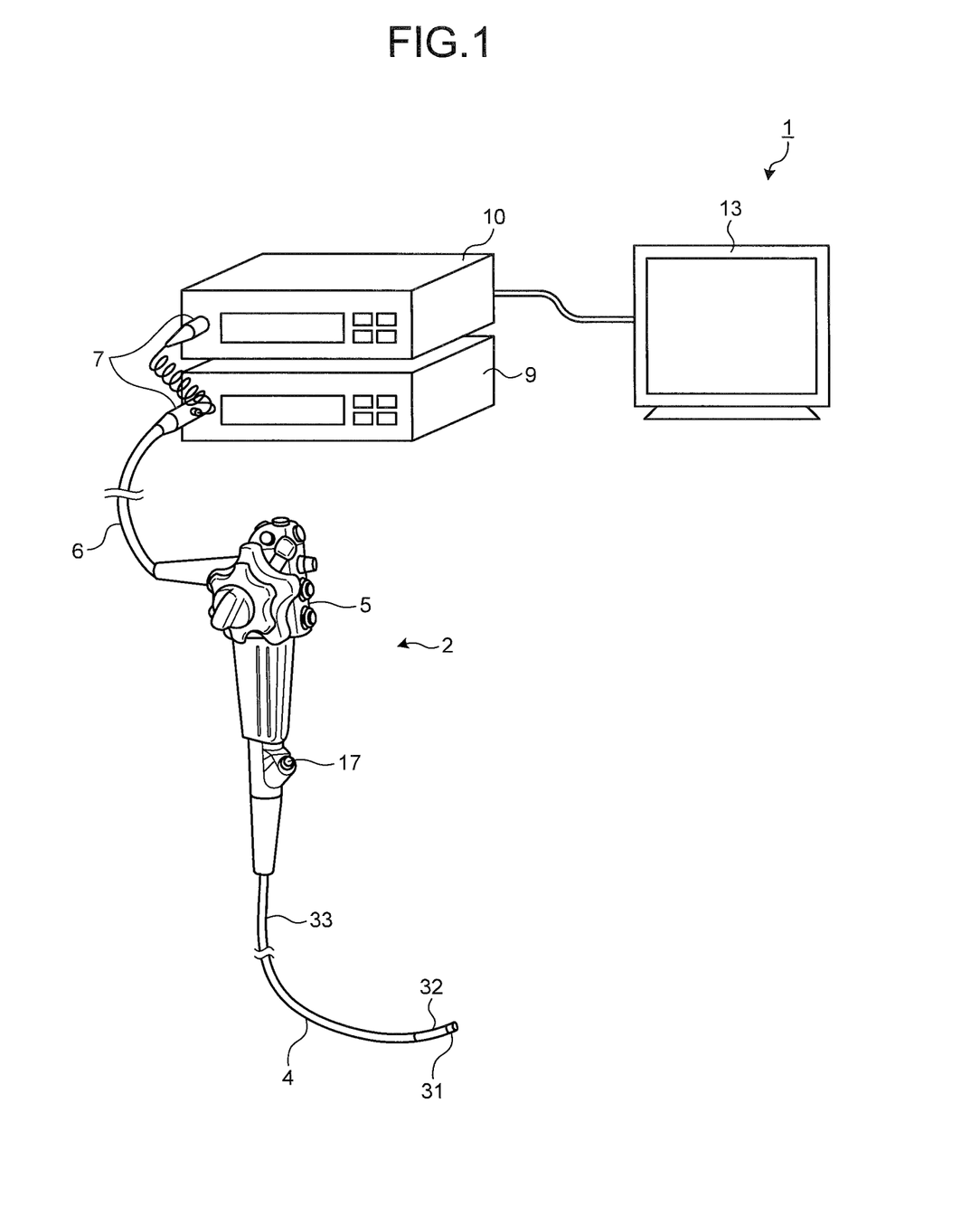
FIG. 1 is a schematic diagram illustrating an overall configuration of an endoscopic system according to a first embodiment of the present invention.

FIG. 1 is a schematic diagram illustrating an overall configuration of an endoscopic system according to an embodiment of the present invention. As illustrated in FIG. 1, an endoscope apparatus 1 includes an endoscope 2, a universal cord 6, connectors 7, a light source device 9, a processor (control device) 10, and a display device 13.

The endoscope 2 is configured to insert an insertion section 4 in a body cavity of a subject to capture an in-vivo image of the subject, and output an imaging signal. The universal cord 6 contains an electric cable bundle, extending to a distal end of the insertion section 4 of the endoscope 2, and connected to an imaging device provided in a distal end portion 31 of the insertion section 4.

The connectors 7 are provided at a proximal end of the universal cord 6, connected to the light source device 9 and the processor 10, each perform predetermined signal processing on the imaging signal output from the imaging device connected to the universal cord 6 and housed in the distal end portion 31, perform analog-digital conversion (A/D conversion) on the imaging signal, and output the imaging signal as an image signal.

The light source device 9, for example, includes a white LED. The light source device 9 emits pulsed white light, and the pulsed white light is emitted, as illumination light, from the distal end of the insertion section 4 of the endoscope 2 to the object through a connector 7 and the universal cord 6.

The processor 10 performs predetermined image processing on the image signal output from the connector 7, and controls the whole of the endoscope apparatus 1. The display device 13 displays the image signal processed by the processor 10.

The insertion section 4 of the endoscope 2 has a proximal end side on which an operating unit 5 is connected, and the operating unit 5 is provided with various buttons or knobs for controlling the functions of the endoscope. The operating unit 5 is provided with a treatment instrument insertion opening 17 for inserting a treatment instrument such as biopsy forceps, an electrosurgical knife, or an inspection probe, into the body cavity of the subject.

The insertion section 4 includes the distal end portion 31 provided with the imaging device, a bending section 32 connected to a proximal end of the distal end portion 31 to be bendable in a plurality of directions, and a flexible tube portion 33 connected to a proximal end of the bending section 32. The bending section 32 is bent by operation of a bending operation knob provided at the operating unit 5, and, for example, bendable in four directions, that is, upward, downward, rightward and leftward, by pulling and releasing a bending wire inserted through the insertion section 4.

In the endoscope 2, a light guide bundle (not illustrated) is disposed for transmitting illumination light from the light source device 9, and an illumination lens (not illustrated) is disposed at an end of the light guide bundle from which illumination light is emitted. This illumination lens is provided in the distal end portion 31 of the insertion section 4 to emit illumination light to the subject.

Figure 2:
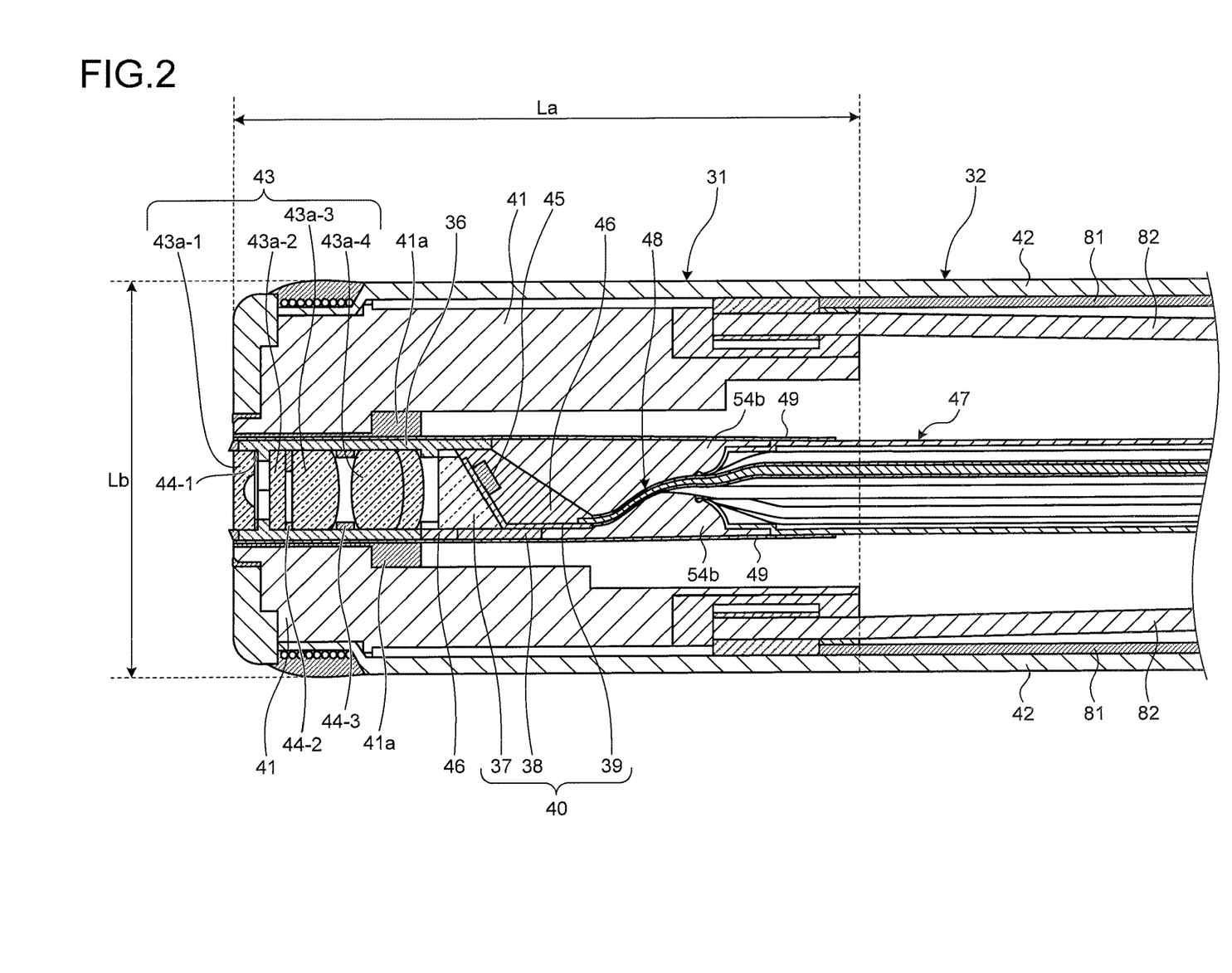
FIG. 2 is a partial cross-sectional view of a distal end of the endoscope illustrated in FIG. 1.

Next, a configuration of the distal end portion 31 of the endoscope 2 will be described in detail. FIG. 2 is a partial cross-sectional view of a distal end of the endoscope 2. FIG. 2 is a cross-sectional view taken along a plane perpendicular to a substrate surface of the imaging device provided in the distal end portion 31 of the endoscope 2, and parallel with an optical axis direction of incident light to the imaging device. FIG. 2 illustrates the distal end portion 31 of the insertion section 4 of the endoscope 2, and part to the bending section 32.

As illustrated in FIG. 2, the bending section 32 is bendable in four directions (i.e., from side to side and up and down), by pulling and releasing a bending wire 82 inserted through a bending tube 81 disposed inside a cladding tube 42 described later. The imaging device is provided in the distal end portion 31 extending from a distal end side of the bending section 32.

The imaging device has a lens unit 43, and an imaging unit 40 disposed on the proximal end side of the lens unit 43, and is bonded to the inside of a distal end body 41 with an adhesive 41a. The distal end body 41 includes a hard member for forming an internal space for housing the imaging device. The distal end body 41 has a proximal end, the outer peripheral portion of which is covered by the cladding tube 42 being flexible. A member located proximally from the distal end body 41 includes a soft member so that the bending section 32 can be bent. The distal end portion 31 in which the distal end body 41 is disposed is formed as a hard portion of the insertion section 4. The hard portion has a length La extending from a distal end of the insertion section 4 to a proximal end of the distal end body 41. Note that, a length Lb corresponds to an outer diameter of the distal end of the insertion section 4.

The lens unit 43 has a plurality of objective lenses 43a-1 to 43a-4, spacers 44-1 to 44-3 disposed between the objective lenses 43a-1 to 43a-4, and an optical member holder 36 for holding the objective lenses 43a-1 to 43a-4, and the optical member holder 36 has a distal end fixedly inserted into the distal end body 41 to be fixed to the distal end body 41.

The imaging unit 40 includes a prism 37 serving as an optical member for reflecting light emitted from the objective lenses 43a-1 to 43a-4 of the lens unit 43, an image sensor 38 for receiving the light reflected from the prism 37, performing photoelectric conversion of the light, and generating an electric signal, and a substrate 39 electrically connected to the image sensor 38. The image sensor 38 is connected to the prism 37 and the substrate 39. On the substrate 39 of the imaging unit 40, an electronic component 45 is mounted which constitutes a drive circuit of the image sensor 38. Furthermore, the substrate 39 has a proximal end to which distal ends of signal cables 48 of an electric cable bundle 47 are connected. Note that, on the substrate 39, electronic components other than the electronic component 45 constituting the drive circuit of the image sensor 38 may be mounted.

Each of the signal cables 48 has a proximal end extending toward the proximal end of the insertion section 4. The electric cable bundle 47 is disposed through the insertion section 4, and extends to the connector 7 through the operating unit 5 and the universal cord 6 illustrated in FIG. 1.

Incident light from one end of the optical member holder 36 is collected by the objective lenses 43a-1 to 43a-4, and made incident to the prism 37. The image sensor 38 is selected from a CCD or CMOS image sensor, or the like, and connected to a position where light emitted from the prism 37 can be received, and converts the received light to the imaging signal. The imaging signal is output to the processor 10 through the signal cable 48 connected to the substrate 39 and the connector 7.

The substrate 39 is a flexible printing circuit board, and bent along the prism 37 and the image sensor 38. The substrate 39 is configured to have a flexible printing circuit board to be bent, so that the length La of the hard portion can be reduced. The electronic component 45 and a connection portion of the signal cable 48 which are mounted on the substrate 39, are sealed with a sealing resin 46.

The imaging unit 40 and the distal end portion of the electric cable bundle 47 are peripherally covered by a heat shrinkable tube 49 for improving resistance. In the heat shrinkable tube 49, an adhesive resin 54b is filled in a gap between components. In the imaging device, an outer peripheral surface of the optical member holder 36, and an outer peripheral surface of a distal end side of the heat shrinkable tube 49 are fixed on an inner peripheral surface of a distal end of the distal end body 41, with the adhesive 41a.

Figure 3:
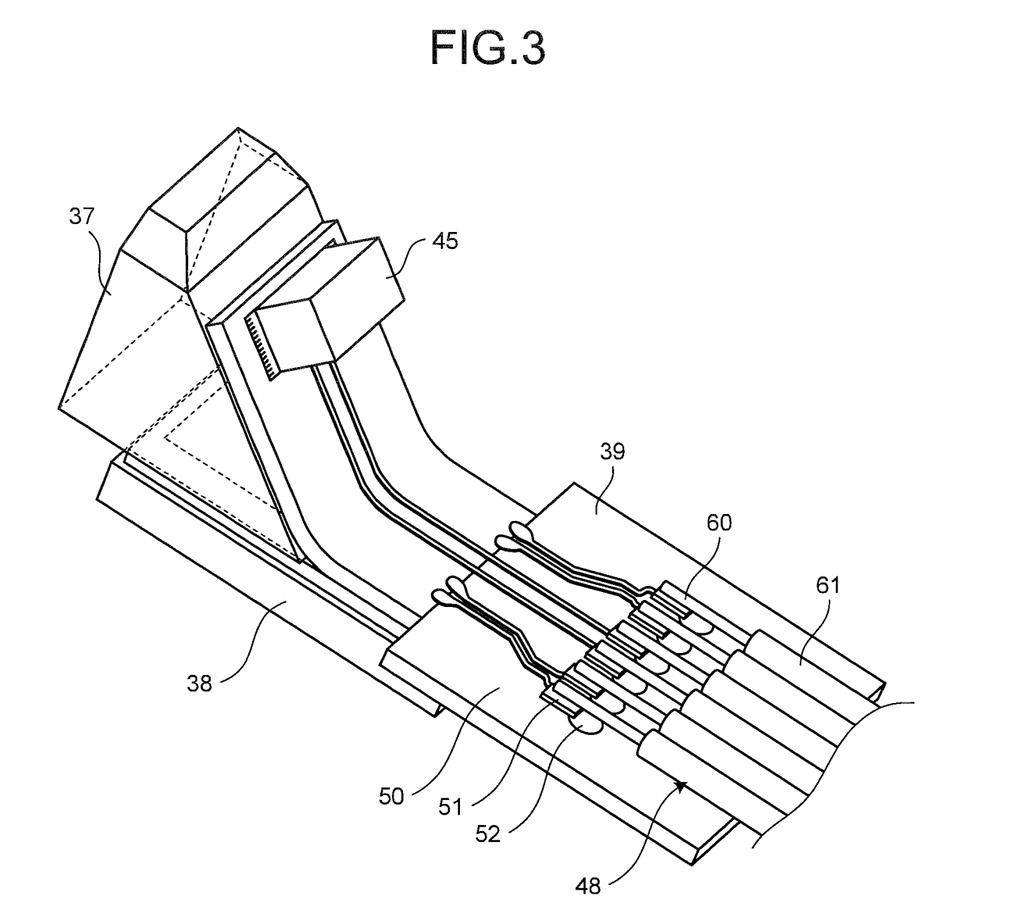
FIG. 3 is a perspective view of a cable connection structure of an imaging device according to the present first embodiment.
Figure 4:
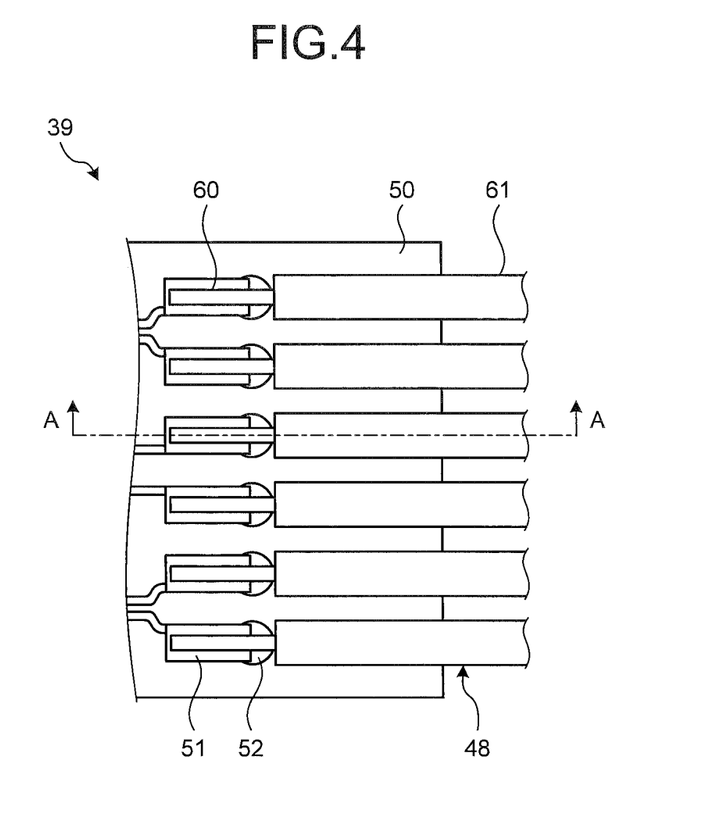
FIG. 4 is a top view of the cable connection structure of FIG. 3.
Figure 5:
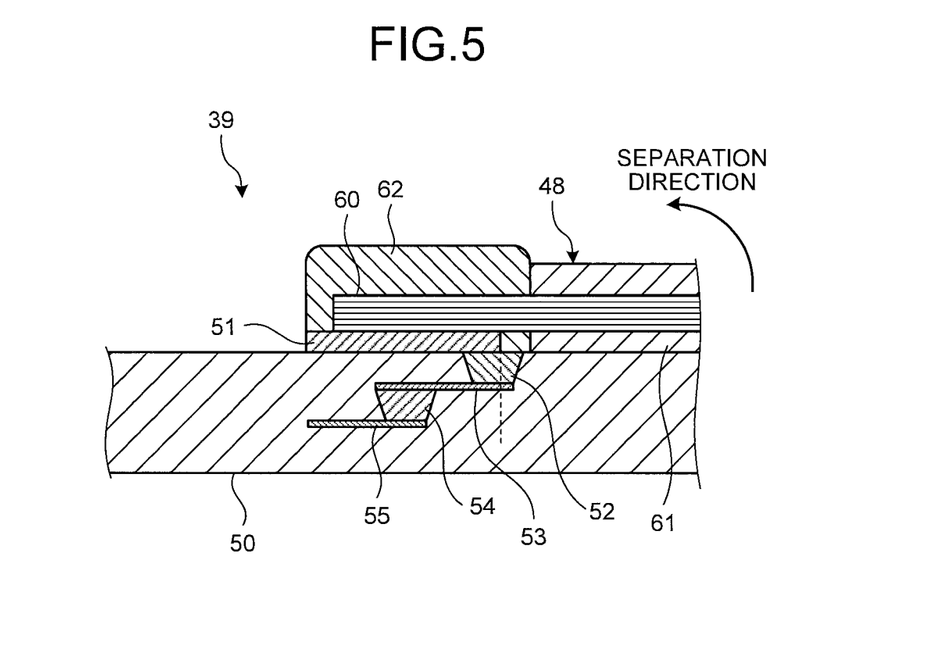
FIG. 5 is a cross-sectional view taken along a line A-A of FIG. 4.

Next, a cable connection structure of the imaging device according to the first embodiment will be described with reference to the drawings. FIG. 3 is a perspective view of the cable connection structure of the imaging device according to the present first embodiment. FIG. 4 is a top view of the cable connection structure of FIG. 3. FIG. 5 is a cross-sectional view taken along a line A-A of FIG. 4. Note that, in FIGS. 3 and 4, solder for connecting the signal cables 48 and electrodes is omitted.

The signal cable 48 has a core 60 covered by a jacket 61 made of an insulating material, and the jacket 61 is separated at an end of the signal cable 48 so as to expose the core 60. The substrate 39 has a base material 50 made of an insulating material such as polyimide, external connection electrodes 51 to which the cores 60 are connected, and vias 52.

The substrate 39 is a multi-layer substrate, and the vias 52 are formed in an uppermost layer. The vias 52 are a wiring via, each of the vias 52 is connected to a via 54 in a next layer with a wiring pattern 53, and the via 54 is connected to a wiring pattern, not illustrated, with a wiring pattern 55. As illustrated in FIGS. 4 and 5, the via 52 is provided at one of both ends of the external connection electrode 51 perpendicular to an axial direction of the signal cable 48, on the proximal end side of the signal cable 48, and the via 52 is formed immediately below an end of the external connection electrode 51. Therefore, even if an external load, in particular a stress, is applied in a separation direction indicated by an arrow in FIG. 5, adhesion strength can be improved at the end of the external connection electrode 51 on which the stress is concentrated, and the external connection electrode 51 can be prevented from being separated from the substrate 39. Further, the via 52 is preferably formed to be displaced so that part of a surface of the via 52 exposed from the substrate 39 does not make contact with the external connection electrode 51, that is, formed so that the end of the external connection electrode 51 on the signal cable 48 side is positioned on a surface of the via 52 exposed from the substrate 39. In particular, the via 52 is preferably formed to be displaced so that substantially half of the surface of the via 52 exposed from the substrate 39 does not make contact with the external connection electrode 51, that is, formed so that the end of the external connection electrode 51 on the signal cable 48 side is positioned above substantially the center of the via 52 exposed from the substrate 39. The surface of the via 52 exposed from the base material 50 without making contact with the external connection electrode 51 is bonded by solder 62 connecting the external connection electrode 51 and the core 60, and the adhesion strength can be further improved.

In the first embodiment, an example of the cable connection structure of the imaging device used in the endoscope apparatus has been described, therefore, the external connection electrodes 51 are formed on the substrate 39, and the signal cables 48 are connected to the external connection electrodes 51, respectively. However, even if the cable connection structure has only one external connection electrode 51, the via 52 provided at one of both ends of the external connection electrode 51 perpendicular to the axial direction thereof, on the proximal end side of the signal cable 48 can improve the adhesion strength at the end of the external connection electrode 51, and the separation of the external connection electrode 51 can be prevented when a stress is applied. Furthermore, the via 52 may be a reinforcing via formed for reinforcement, in spite of the wiring via.

Second Embodiment

Figure 6:
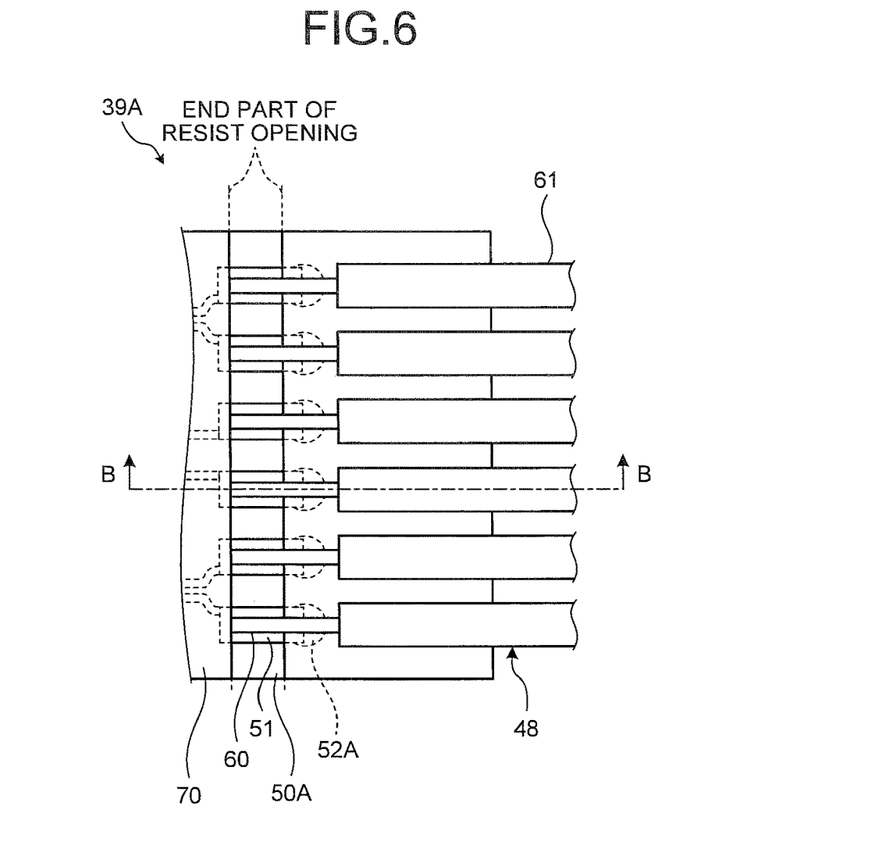
FIG. 6 is a top view of a cable connection structure according to a second embodiment of the present invention.
Figure 7:
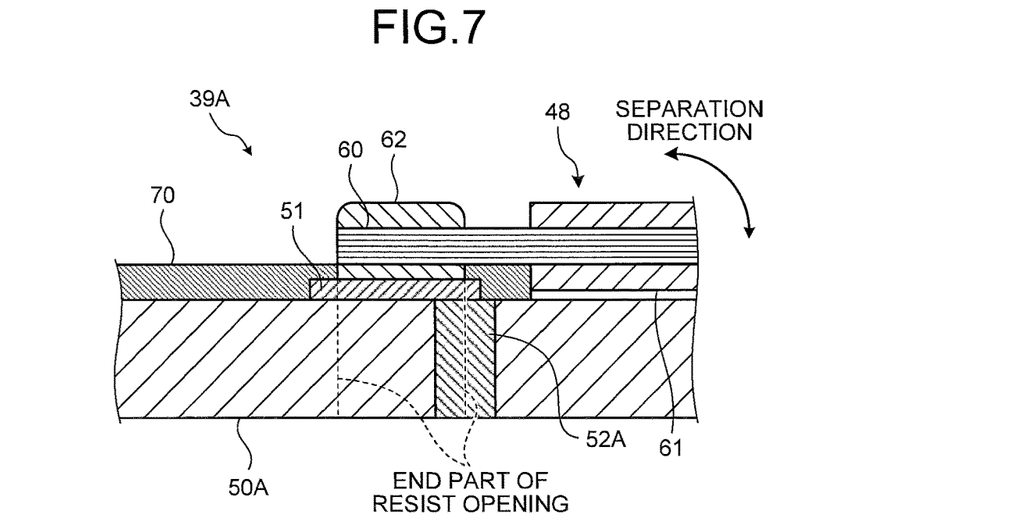
FIG. 7 is a cross-sectional view taken along a line B-B of FIG. 6.

In a cable connection structure according to a second embodiment, a solder resist layer is formed on the base material to cover both ends of the external connection electrode perpendicular to the axial direction of the signal cable. FIG. 6 is a top view of the cable connection structure according to the second embodiment of the present invention. FIG. 7 is a cross-sectional view taken along a line B-B of FIG. 6. Note that, in FIG. 6, solder for connecting the signal cables and electrodes is omitted.

As illustrated in FIGS. 6 and 7, a solder resist layer 70 is formed, as an over resist structure, on a base material 50A to cover both ends of the external connection electrode 51 perpendicular to the axial direction of the signal cable 48.

Furthermore, vias 52A are formed such that each of the vias 52A is provided at one of both ends of the external connection electrode 51 perpendicular to the axial direction of the signal cable 48, on the proximal end side of the signal cable 48. The via 52A is the reinforcing via formed to penetrate the base material 50A. The via 52A is the reinforcing via only provided for reinforcement of the external connection electrode 51, but the wiring via electrically connected to another member may be employed, or a via formed only in one layer of the multi-layer substrate may be employed.

In the second embodiment, the via 52A is provided at one of the both ends of the external connection electrode 51 perpendicular to the axial direction of the signal cable 48, on the proximal end side, the solder resist layer 70 is formed to cover both ends of the external connection electrode 51, perpendicular to the axial direction of the signal cable 48, so that the adhesion strength can be improved at the end of the external connection electrode 51 on which the stress is concentrated, and separation of the external connection electrode 51 can be prevented. Furthermore, the end of the external connection electrode 51 is formed at a position where substantially half of an exposed surface of the via 52A exposed from the base material 50A does not make contact with the external connection electrode 51, the surface of the via 52A exposed from the base material 50A without making contact with the external connection electrode 51 is bonded to the solder resist layer 70 covering the end of the external connection electrode 51, and adhesion strength can be further improved.

Note that, in the second embodiment, the solder resist layer 70 is formed to cover both ends of the external connection electrode 51, positioned perpendicular to the axial direction of the signal cable 48, but the solder resist layer may be formed to cover four sides of the external connection electrode 51.

Figure 8:
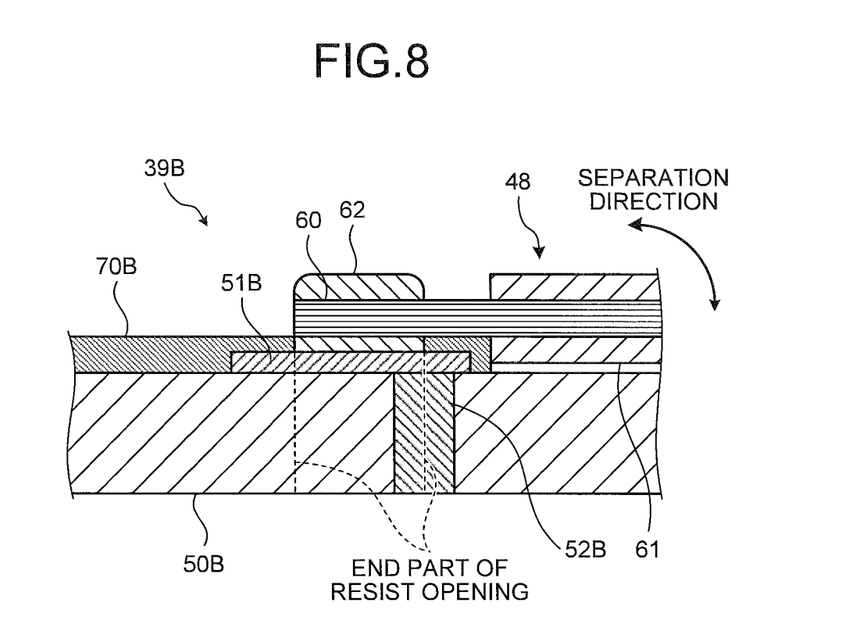
FIG. 8 is a cross-sectional view of a cable connection structure according to a modification of the second embodiment of the present invention.

The via may be formed in a lower part of an opening end of the solder resist layer, as long as the via is located at one of both ends of the external connection electrode 51 perpendicular to the axial direction of the signal cable 48. FIG. 8 is a cross-sectional view of a cable connection structure according to a modification of the second embodiment of the present invention. According to a modification of the second embodiment, a solder resist layer 70B is formed on a base material 50B to cover both ends of an external connection electrode 51B perpendicular to the axial direction of the signal cable 48. A via 52B is formed in the lower part of the opening end of the solder resist layer 70B, on a proximal end side of the external connection electrode 51B perpendicular to the axial direction of the signal cable 48.

According to the modification of the second embodiment, both ends of the external connection electrode 51B perpendicular to the axial direction of the signal cable 48 are covered, from an end, longer than that in the second embodiment by the solder resist layer 70B, the via 52B is formed in the lower part of the open end of the solder resist layer 70B, on a proximal end side of the external connection electrode 51B perpendicular to the axial direction of the signal cable 48, and the adhesion strength can be improved at the end of the external connection electrode 51B.

Third Embodiment

Figure 9:
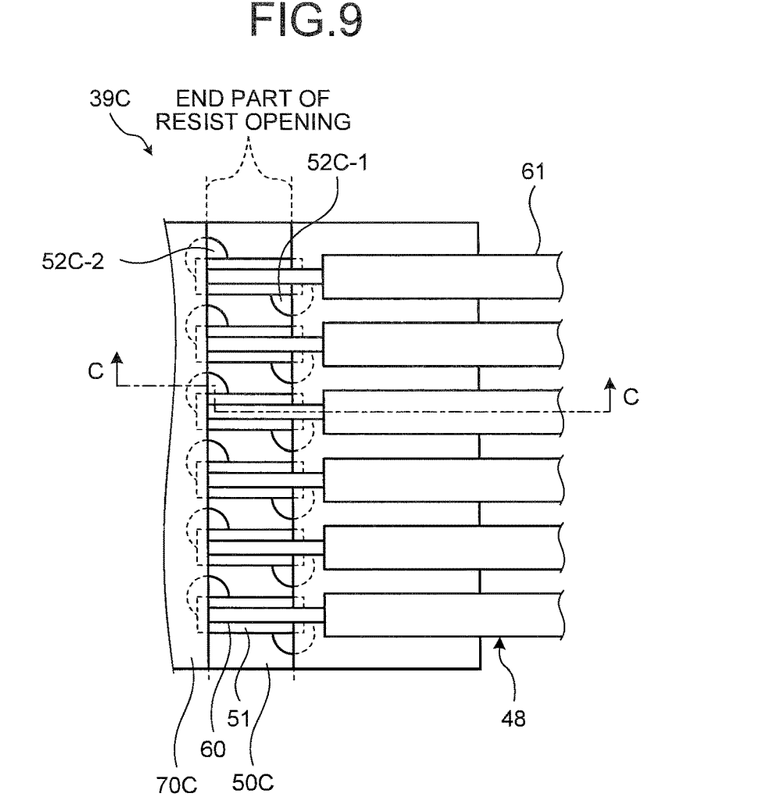
FIG. 9 is a top view of a cable connection structure according to a third embodiment of the present invention.
Figure 10:
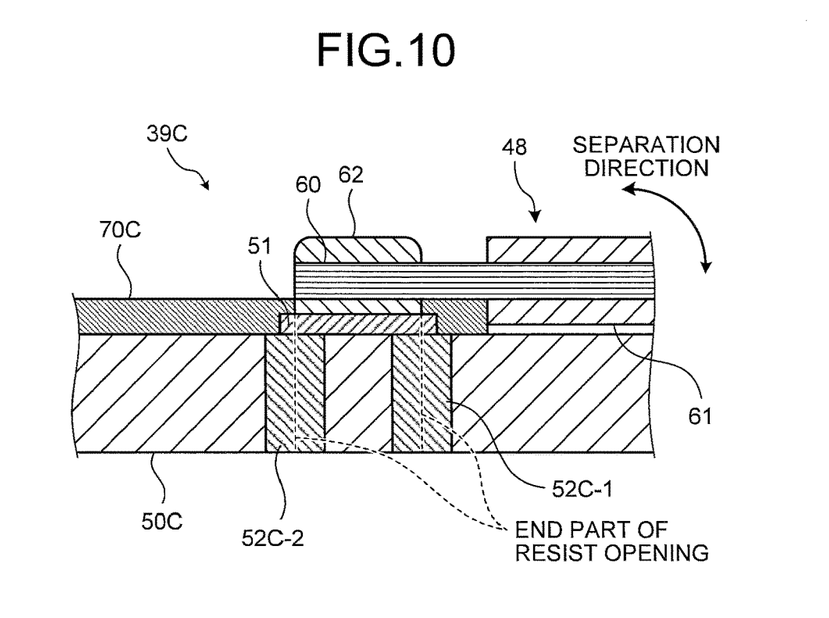
FIG. 10 is a cross-sectional view taken along a line C-C of FIG. 9.

In a cable connection structure according to a third embodiment, vias are provided at both ends of the external connection electrode 51 perpendicular to the axial direction of the signal cable 48. FIG. 9 is a top view of the cable connection structure according to the third embodiment of the present invention. FIG. 10 is a cross-sectional view taken along a line C-C of FIG. 9. Note that, in FIG. 9, solder for connecting the signal cables and the electrodes is omitted.

As illustrated in FIGS. 9 and 10, a solder resist layer 70C is formed, as an over resist structure, on a base material 50C to cover both ends of the external connection electrode 51 perpendicular to the axial direction of the signal cable 48.

Furthermore, a via 52C-1 and a via 52C-2 are provided at both ends of the external connection electrode 51 perpendicular to the axial direction of the signal cable 48, on the proximal end side and the other end side of the signal cable 48. The via 52C-1 and via 52C-2 formed on the proximal end side and the other end side of the signal cable 48 are preferably provided symmetrically on a diagonal line of the external connection electrode 51. Since the via 52C-1 and the via 52C-2 are provided symmetrically on the diagonal line of the external connection electrode 51, even when a shear stress is applied to the connection portion, separation of the external connection electrode 51 can be prevented. Note that, in FIG. 9, the via 52C-1 and the via 52C-2 are provided symmetrically on the diagonal line of the external connection electrode 51, but the via 52C-1 and the via 52C-2 are not limited to the above description, and may be provided symmetrically to a center line of the external connection electrode 51 perpendicular to the axial direction of the signal cable 48.

In the third embodiment, the via 52C-1 and the via 52C-2 are provided at both ends of the external connection electrode 51 perpendicular to the axial direction of the signal cable 48, and the solder resist layer 70C is formed to cover both ends of the external connection electrode 51 perpendicular to the axial direction of the signal cable 48, and thus, the adhesion strength can be improved at the end of the external connection electrode 51 on which the stress is concentrated, and separation of the external connection electrode 51 can be prevented. The both ends of the external connection electrode 51 perpendicular to the axial direction of the signal cable 48 are located on surfaces of the via 52C-1 and the via 52C-2 exposed from the base material 50C, a part of the surface of the via 52C-1 or the via 52C-2 exposed from the base material 50C without making contact with the external connection electrode 51 is bonded to the solder resist layer 70C covering an end of the external connection electrode 51. With this structure, adhesion strength can be further improved.

Fourth Embodiment

Figure 11:
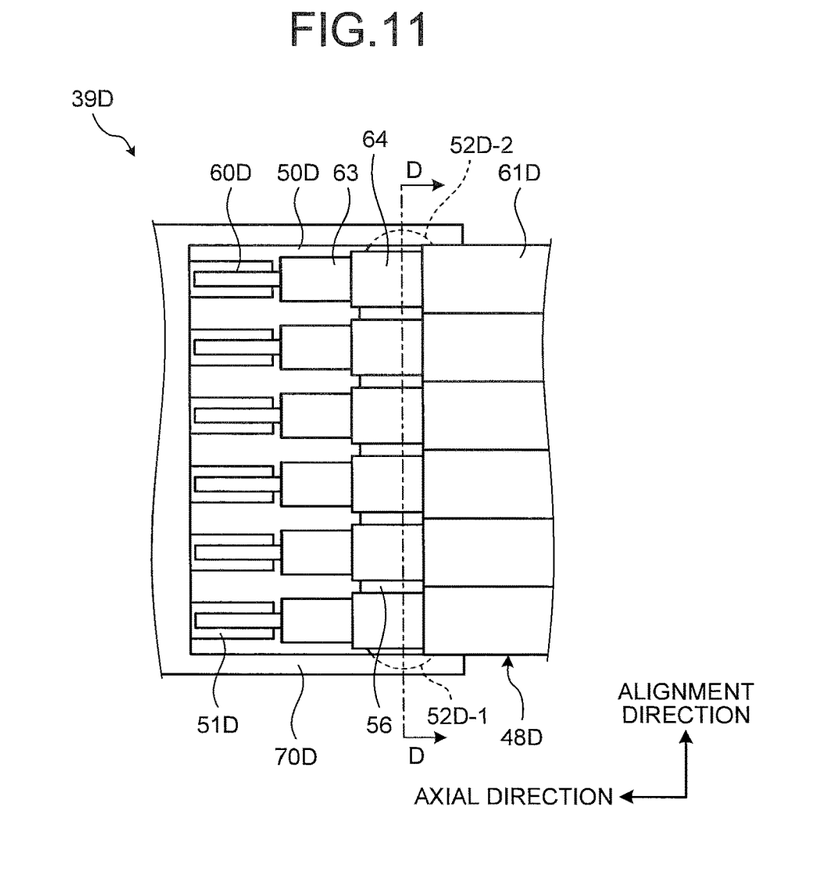
FIG. 11 is a top view of a cable connection structure according to a fourth embodiment of the present invention.
Figure 12:
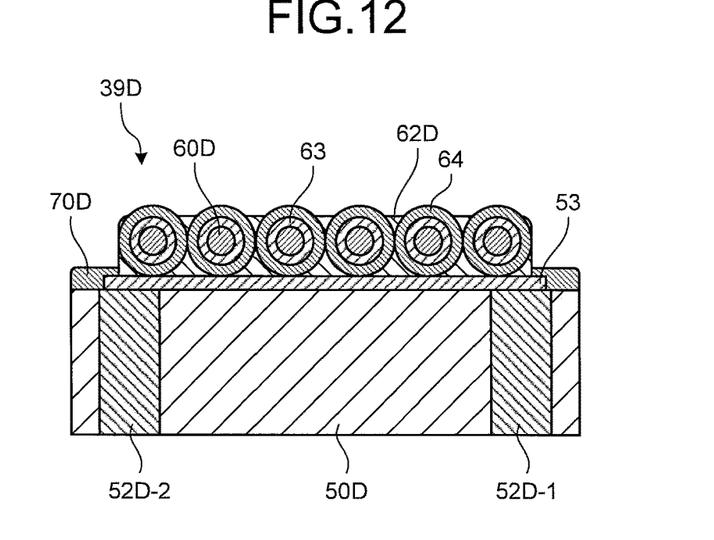
FIG. 12 is a cross-sectional view taken along a line D-D of FIG. 11.
Figure 13:
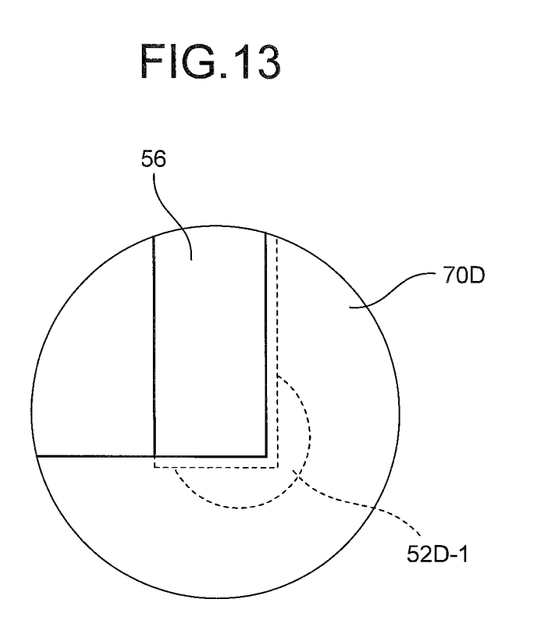
FIG. 13 is a diagram illustrating a layered relationship between a via, a shield connection electrode, and a solder resist layer.

A fourth embodiment represents a cable connection structure in which coaxial cables are connected to a substrate. FIG. 11 is a top view of the cable connection structure according to the fourth embodiment of the present invention. FIG. 12 is a cross-sectional view taken along a line D-D of FIG. 11. FIG. 13 is a diagram illustrating a layered relationship between a via, a shield connection electrode, and a solder resist layer. Note that, in FIG. 11, solder for connecting the signal cables and electrodes is omitted.

In the cable connection structure according to the fourth embodiment, each of coaxial cables 48D has a core 60D including an electrically conductive material, an inner insulating material 63 for covering an outer periphery of the core 60D, a shield 64 for covering an outer periphery of the inner insulating material 63, and a jacket 61D being an outer insulating material for covering an outer periphery of the shield 64, and the coaxial cable 48D is connected to a substrate 39D. The coaxial cable 48D has an end at which layers are removed to expose the core 60D, the inner insulating material 63, and the shield 64.

A plurality of core connection electrodes 51D for connecting a plurality of cores 60D of the coaxial cables 48D, and one shield connection electrode 56 connected with a plurality of shields 64 are provided on the substrate 39D. In the fourth embodiment, the vias for improving the adhesion strength of the electrode are only provided at both ends of the shield connection electrode 56.

A solder resist layer 70D is formed on a base material 50D, and covers an end side of the side of the coaxial cable 48D of both ends of a core connection electrode 51D perpendicular to an axial direction of the coaxial cable 48D, and a proximal end side of the coaxial cable 48D of both ends of the shield connection electrode 56 perpendicular to the axial direction of the coaxial cable 48D, and further covers both ends of the shield connection electrode 56 parallel with the axial direction of the coaxial cable 48D.

A via 52D-1 and a via 52D-2 face each other at both ends of the shield connection electrode 56 parallel with the axial direction of the coaxial cables 48D. The via 52D-1 and the via 52D-2 are formed at positions where at least part of surfaces of the via 52D-1 and the via 52D-2 exposed from the base material 50D do not make contact with the shield connection electrode 56. For example, as illustrated in FIG. 13, the via 52D-1 is formed from a position immediately below the shield connection electrode 56 toward a proximal end side of the position coaxial cable 48D, and a position displaced outside a side of the shield connection electrode 56 parallel with the axial direction of the coaxial cable 48D. Part of the exposed surfaces of the via 52D-1 and the via 52D-2 are formed at positions where the surfaces do not make contact with the shield connection electrode 56, and the surfaces of the via 52D-1 and the via 52D-2 exposed from the base material 50D without making contact with the shield connection electrode 56 are bonded to the solder resist layer 70D covering the ends of the shield connection electrode 56, and thus, adhesion strength can be further improved.

According to some embodiments, a wiring via and/or a reinforcing via is provided at least at one of both ends of an electrode perpendicular to an axial direction of a cable, on the proximal end side of the cable. With this structure, even if a stress is applied to a connection portion between the electrode and the cable on the substrate, it is possible to prevent separation of the electrode from the substrate.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

1 ENDOSCOPE APPARATUS
2 ENDOSCOPE

4 INSERTION SECTION
5 OPERATING UNIT
6 UNIVERSAL CORD
7 CONNECTOR
9 LIGHT SOURCE DEVICE
10 PROCESSOR
13 DISPLAY DEVICE
17 TREATMENT INSTRUMENT INSERTION OPENING
31 DISTAL END PORTION
32 BENDING SECTION
33 FLEXIBLE TUBE PORTION
36 OPTICAL MEMBER HOLDER
37 PRISM
38 IMAGE SENSOR
39, 39A, 39B, 39C, 39D SUBSTRATE
40 IMAGING UNIT
41 DISTAL END BODY
41a ADHESIVE
42 CLADDING TUBE
43 LENS UNIT
43a-1 to 43a-4 OBJECTIVE LENS
44-1 to 44-3 SPACER
45 ELECTRONIC COMPONENT
46 SEALING RESIN
47 ELECTRIC CABLE BUNDLE
48 SIGNAL CABLE
48D COAXIAL CABLE
49 HEAT SHRINKABLE TUBE
50 BASE MATERIAL
51 EXTERNAL CONNECTION ELECTRODE
51D CORE CONNECTION ELECTRODE
52, 54 VIA
53, 55 WIRING PATTERN
54b ADHESIVE RESIN
56 SHIELD CONNECTION ELECTRODE
60, 60D CORE
61, 61D JACKET
62, 62D SOLDER
63 INNER INSULATING MATERIAL
64 SHIELD
70 SOLDER RESIST LAYER

What is claimed is:

1. A cable connection structure comprising:
   a cable having a core and a jacket made of an insulating material to cover the core, the cable having an exposed portion of the core at a distal end of the cable; and
   a substrate connected with the exposed portion of the core, wherein
   the substrate comprises:
      a base material made of an insulating material;
      an external connection electrode formed on a surface of the base material and connected with the exposed portion of the core; and
      a via provided in the base material and having an end exposed from a mounting surface of the substrate on which the cable is mounted, the via being connected with the external connection electrode, wherein
   the via is provided on one end side of the external connection electrode, the one end side being offset proximally from the distal end of the cable in an axial direction of the cable,
   a part of a surface of the via exposed from the substrate does not contact with the external connection electrode;
   the one end side of the external connection electrode is located at a substantial center of the via exposed from the substrate, and
   the substrate further comprises a solder resist layer on the base material so as to cover the one end side of the external connection electrode and an other end side of the external connection electrode and to cover the part of the surface of the via exposed from the substrate.

2. The cable connection structure according to claim 1, wherein
   the via comprises a first via and the substrate further comprises a second via in the base material,
   the second via is provided symmetrically with regard to the first via on a diagonal line of the external connection electrode.

3. The cable connection structure according to claim 1, wherein:
   the cable comprises a plurality of cables,
   the external connection electrode comprises a plurality of external connection electrodes respectively corresponding to the plurality of cables, and
   the plurality of cables are respectively connected to the plurality of external connection electrodes.

4. The cable connection structure according to claim 3, wherein the plurality of cables comprise a plurality of coaxial cables each having:
   an inner core made of an electrically conductive material;
   an inner insulating material for covering an outer periphery of the inner core;
   a shield for covering an outer periphery of the inner insulating material; and
   an outer insulating material for covering an outer periphery of the shield,
   the substrate further comprises:
      a second via in the base material;
      a plurality of core connection electrodes respectively connected with the inner cores of the plurality of coaxial cables; and
      one shield connection electrode connected with the shields of the plurality of coaxial cables, and
   the via and the second via are provided so as to face each other at both ends of a surface of the shield connection electrode parallel with an axial direction of each of the plurality of coaxial cables.

5. An endoscope apparatus comprising an imaging device configured to be inserted into a living body to image an inside of the living body, wherein the imaging device comprises the cable connection structure according to claim 1.

6. A cable connection structure comprising:
   a cable having a core and a jacket made of an insulating material to cover the core, the cable having an exposed portion of the core at a distal end of the cable; and
   a substrate connected with the exposed portion of the core, wherein
   the substrate comprises:
      a base material made of an insulating material;
      an external connection electrode formed on a surface of the base material and connected with the exposed portion of the core; and
      a via provided in the base material and having an end exposed from a mounting surface of the substrate on which the cable is mounted, the via being connected with the external connection electrode, wherein
   the via is provided on one end side of the external connection electrode, the one end side being offset proximally from the distal end of the cable in an axial direction of the cable,
   a part of a surface of the via exposed from the substrate does not contact with the external connection electrode;

the one end side of the external connection electrode is located at a substantial center of the via exposed from the substrate, and the substrate further comprises solder for connecting the external connection electrode with the core, and the part of the surface of the via exposed from the substrate contacts with the solder.

\* \* \* \* \*